United States Patent [19]
Grendelmeier

[11] Patent Number: 5,943,114
[45] Date of Patent: Aug. 24, 1999

[54] EYEGLASSES WITH ATTACHABLE PROTECTIVE SHIELD

[76] Inventor: Alexander Grendelmeier, Birkenweg 12, 4663 Aarburg, Switzerland

[21] Appl. No.: 09/027,347

[22] Filed: Feb. 20, 1998

[30] Foreign Application Priority Data

Feb. 26, 1997 [EP] European Pat. Off. .............. 97810104

[51] Int. Cl.[6] ....................................... G02C 9/00
[52] U.S. Cl. ................................. 351/47; 351/57
[58] Field of Search ................... 351/47, 57, 48, 351/58, 41, 44

[56] References Cited

U.S. PATENT DOCUMENTS

| | | | |
|---|---|---|---|
| 5,428,407 | 6/1995 | Sheffield | 351/58 |
| 5,614,963 | 3/1997 | Parker | 351/47 |

FOREIGN PATENT DOCUMENTS

| | | |
|---|---|---|
| 2.224.121 | 10/1974 | France . |
| 93 12 039.7 | 10/1993 | Germany . |
| WO 92/10777 | 6/1992 | WIPO . |

*Primary Examiner*—Hung Xuan Dang
*Attorney, Agent, or Firm*—Seed and Berry LLP

[57] ABSTRACT

A protective shield can be put on eyeglasses comprising a frame and lenses held therein. For this purpose the protective shield is provided with two pins, which are introduced into slot-shaped recesses of the eyeglass frame, whereas in the middle area of the protective shield a central pin is provided which can be inserted into a central slot-shaped recess. Achieved by means of this device is an optimal fit of the protective shield placed on the eyeglasses, optimal protective glasses being created. Advantageous hereby is that both with the protective shield and also without it, one has completely functional glasses, which can be used in various ways.

6 Claims, 2 Drawing Sheets

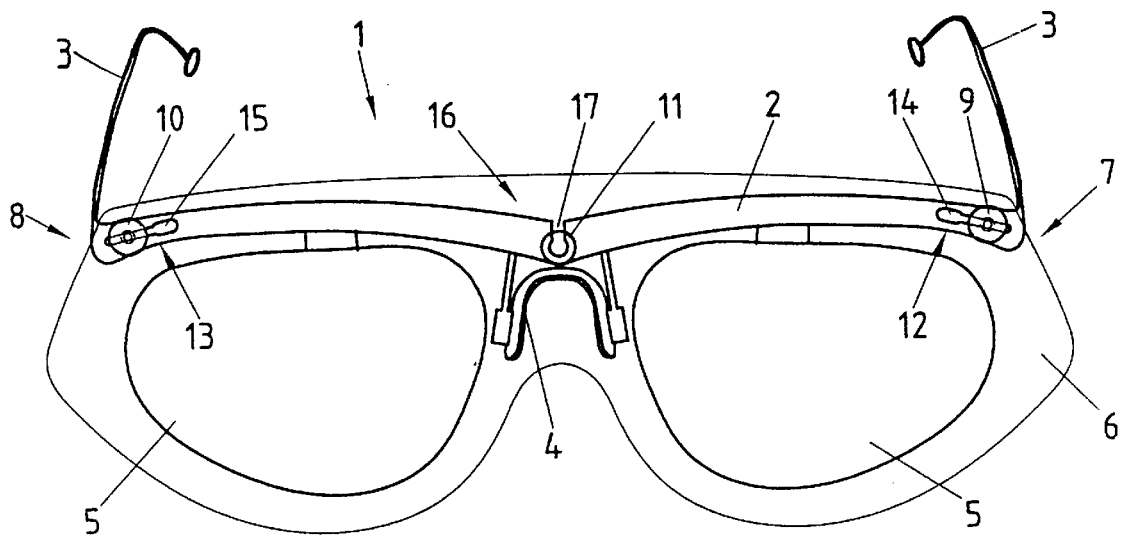
FIG. 1
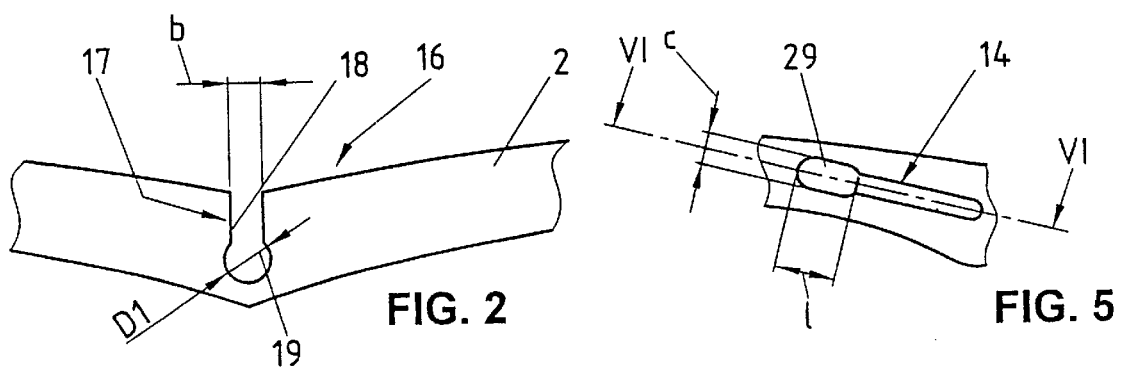
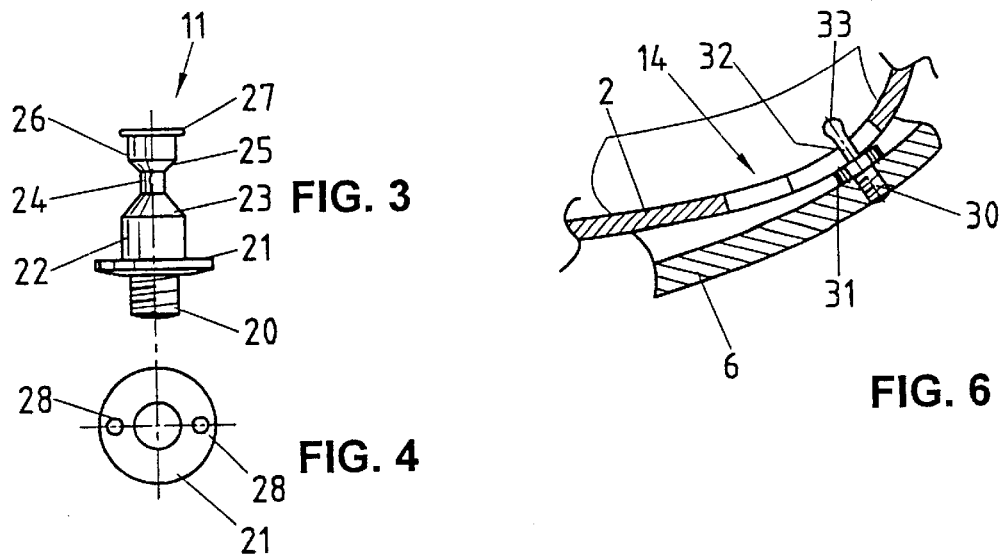

EYEGLASSES WITH ATTACHABLE PROTECTIVE SHIELD

TECHNICAL FIELD

This invention relates to eyeglasses with an attachable protective shield.

BACKGROUND OF THE INVENTION

Eyeglasses on which additional lenses can be placed, for example as sun protection, are known. These lenses are roughly the same size as the prescription lenses of the eyeglasses and are held in a bearing part. Provided on this bearing part are hooks or clips so that the part with the sunglass lenses can be clipped onto the eyeglasses. The sunglass lenses then come to lie on the prescription lenses, the hooks supporting themselves in a clamping fashion on the back part of the prescription lenses or respectively on the frame.

The holding of the aforementioned protective lenses is not optimal, in particular when eyeglasses provided with such protective lenses are to be worn for various kinds of sports. Moreover the protective function of these clip-on lenses is not optimal since they usually are only approximately the same size as the eyeglasses, and sizes of eyeglasses change of course with fashion trends. Particularly in the case of small lenses, the protection against the sun, for example, is insufficient. Moreover eyeglasses so equipped are also unsuitable as a wind protection for the eyes. In addition, such devices often leave something to be desired with respect to aesthetic appearance.

Sport glasses are also known which offer good protection for the eyes against sun and wind. These glasses usually have a wrap-around protective lens of convex shape, which is not suitable, however, for the correction of defective vision. Therefore to correct vision, insets with the corresponding prescription lenses are then used. Such glasses are well suited for all kinds of sports; the protection against sun and wind is optimal. If, however, a person wearing such glasses enters a closed room after being in the sun, for example, nothing can be seen with these glasses since the room is too dark. Thus these sunglasses with the prescription inset must be removed and replaced by a normal pair of glasses. It is therefore necessary to carry around a second, normal pair of eyeglasses in addition to the sports sunglasses with the prescription lens inset. Moreover, since protective eyeglasses with prescription insets are rather expensive, owning such sports glasses becomes a financial question.

SUMMARY OF THE INVENTION

The object of the present invention is thus to create eyeglasses with an attachable protective shield which offer at the same time optimal protection against sun and wind, for example, a simple placement of the protective shield on the eyeglasses being possible and the connection between the eyeglasses and the protective shield being optimal.

This object is achieved according to the invention by means of eyeglasses with attachable protective shield comprising: an eyeglass frame with prescription lenses held in the frame, holding means disposed on the attachable protective shield and/or on the eyeglass frame, with which means the protective shield is held on the eyeglass frame in front of the lenses and essentially parallel thereto, wherein the holding means comprise at least two pins, which are inserted into the protective shield and are protruding and which are provided with a swelling on the area turned away from the protective shield, and at least two slot-shaped recesses are provided in the frame corresponding to the pins inserted on the protective shield, which recesses are each provided with an extension, and wherein the eyeglass frame and the attachable protective shield are elastically tensioned with respect to each other.

In addition these glasses, which can be worn alone or with attached protective shield, should fulfil the wearer's demands with respect to aesthetic appearance.

To obtain an optimal attachment of the protective shield to the eyeglasses, the holding means preferably consists of two pins laterally mounted and a central pin, all of which are held in corresponding slot-shaped recesses provided on the eyeglass frame.

To attach the protective shield to the eyeglasses or respectively to insert the pins into the recesses provided on the eyeglass frame, the protective shield is pressed in the middle area against the eyeglass frame after the two lateral pins have been introduced into the corresponding recesses, an elastic shaping taking place, while the central pin is introduced into the central recess. In springing back, the swelling on the central pin engages in a corresponding widening of the slot-shaped recess. The fit of the protective shield on the eyeglasses is thus practically without any play. The retention force acting upon the central pin will increase even more when the eyeglasses are being worn.

The two lateral pins and the central pin are preferably screwed into threaded bores provided on the protective shield. To this end the pins have, in addition to a screw part, a flange-shaped supporting part, on which in each case two bores have been made on the side turned away from the protective shield. These bores serve as places where a suitably designed tool can be inserted, with which the pins can be easily screwed into the protective shield.

If the protective shield is to be used as a protection against the sun, it will to be suitably tinted. It is of course also possible to make the protective shield out of clear material and to place it on the eyeglasses so that it protects the eyes from shavings during machining, for example.

BRIEF DESCRIPTION OF THE DRAWINGS

An embodiment of the eyeglasses with attached protective shield according to the invention will be more closely described in the following, by way of example, with reference to the attached drawing. Shown are:

FIG. 1, a view from the front of eyeglasses with attached protective shield according to the invention;

FIG. 2, a depiction of the central, slot-shaped recess in the eyeglass frame;

FIG. 3, a view of the central pin;

FIG. 4, a view from above of the central pin according to FIG. 3;

FIG. 5, a depiction of a lateral, slot-shaped recess in the eyeglass frame,

FIG. 6, a section through the eyeglass frame along line VI—VI of FIG. 5 with attached protective shield;

DETAILED DESCRIPTION OF THE INVENTION

Figure 7:
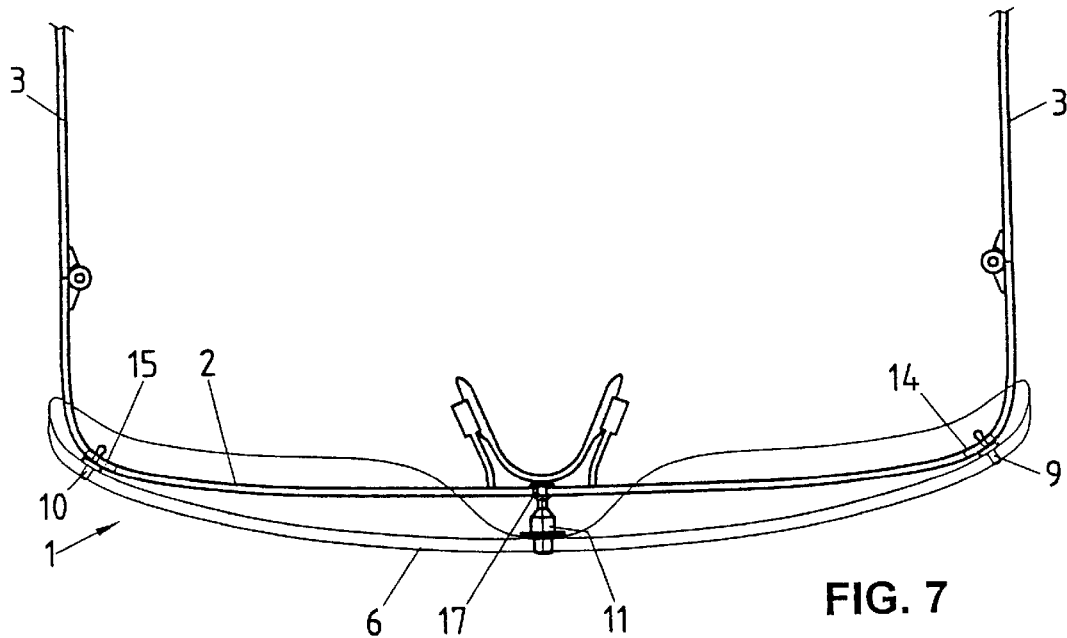
FIG. 7, a view from above of the eyeglasses with attached protective shield according to the invention.

Shown in FIG. 1 are eyeglasses 1 comprising an eyeglass frame 2 with articulated clips, a nose piece 4 and prescription lenses 5. The eyeglass lenses 5 can hereby be connected in such a way that they can be detached and exchanged, such as is described, for example, in EP-A-0 514 514.

Placed on the eyeglasses 1 is a protective shield 6. This protective shield 6 is made, for example, of an acrylic glass, which can be clear or tinted, depending upon whether this protective shield 6 is used to protect the eyes against flying particles, for example shavings during machining of workpieces, to protect against wind in bad weather or as an additional protection against the sun. Inserted into this protective shield are one pin, 9 or 10, on each side in a lateral edge area, 7, 8. A central pin 11 is inserted in the protective shield 6 approximately in the middle between these two pins 9 and 10.

One lateral slot-shaped recess 14 or 15, respectively, is made in the eyeglass frame 2 in the lateral edge areas 12 and 13, while a central, slot-shaped recess 17 is provided in the middle area 16 of the eyeglass frame 2. If the protective shield 6 is placed on the eyeglasses 1, the pins 9 or 10, respectively, are held in the corresponding lateral slot-shaped recesses 14 or 15, respectively, while the central pin 11 is held in the central slot-shaped recess 17 of the eyeglass frame 2, as will be described more precisely in the following.

Shown in FIG. 2 is the central area 16 of the eyeglass frame 2. Visible here is the central, slot-shaped recess 17. This central, slot-shaped recess 17 runs essentially transversely to the eyeglass frame 2. The central slot-shaped recess 17, which is open toward the upper edge of the eyeglass frame 2, has a narrowing 18 and a bore 19 adjoining the narrowing. The narrowing 18 has a width b, while the diameter of the bore is D1.

When the protective shield has been placed on, the central pin 11 comes to lie in the central, slot-shaped recess 17 of the eyeglass frame 2, as is shown in FIGS. 3 and 4. This central pin 11 has a screw part 20, which can be screwed into the protective shield 6, a flange-shaped supporting part 21, a first cylindrical part 22, a tapering first frustum 23, a second cylindrical part 24, a widening second frustum 25 and a third cylindrical part 26 adjoining thereto, which is terminated with a collar 27. As can be seen in FIG. 4, two bores are provided on the flange-shaped supporting part 21 in which a suitably designed tool can be inserted, by means of which the central pin 11 can be screwed into the protective shield 6.

Upon placing of the protective shield 6 on the eyeglasses 1, the central pin 11 with its second cylindrical part 24, whose diameter is smaller than the width b of the narrowing 18, is inserted all the way into the bore 19 of the central, slot-shaped recess 17. The first frustum 23 and the second frustum 25 serve hereby as insertion aids. As will be seen later, when placed on the eyeglasses 1, the protective shield 6 springs away from the eyeglass frame 2, so that the third cylindrical part 26 of the central pin 11 is pulled into the bore 19 of the central, slot-shaped recess 17 until the collar 27 is supported on the surface of the eyeglass frame 2. The central pin 11 is thus held securely in the central, slot-shaped recess 17.

As can be seen in FIG. 5, the lateral slot-shaped recesses 14 and 15, which are made in the lateral edge areas 12 and 13 of the eyeglass frame 2, have extensions 29, whereby only the lateral slot-shaped recess 14 is shown, whereas the lateral slot-shaped recess 15 is disposed in mirror image. This extension 29 has in each case a width c and a length I.

The pin 9 provided on the protective shield 6 comes to lie in this lateral slot-shaped recess 14 when the protective shield 6 is placed on the eyeglasses 1, as shown in FIG. 6. The pin 9 is made up of a screw portion 30, a flange-shaped supporting portion 31 and a cylindrical portion 32, which is terminated with a spherical swelling 33. Here, too, the flange-shaped supporting part 31 has bores which correspond to the bores 28 of the central pin 11, shown in FIG. 4. With these the pin 9 can likewise be screwed into the protective shield 6. Correspondingly designed is the pin 10, which comes to lie in the slot-shaped recess 15.

When placing the protective shield 6 on the eyeglasses 1, the swelling 33 is led through the extension 29 of the lateral, slot-shaped recess 14, whereby, according to FIG. 5, the width c is slightly greater, and the length I greater, than the swelling 33 of the pin 9. In the state where the protective shield 6 is placed on the eyeglasses 1, the pin 9 with its cylindrical part 32 is located in the area of the lateral slot-shaped recess 14 adjoining the extension 29, which has a width which is less than the diameter of the swelling 33. Thus also the lateral area of the protective shield 6 is held optimally on the eyeglasses 1. It is clear that the second pin 10 on the other side of the protective shield 6 is inserted and held correspondingly in the lateral, slot-shaped recess 15.

Figure 8:
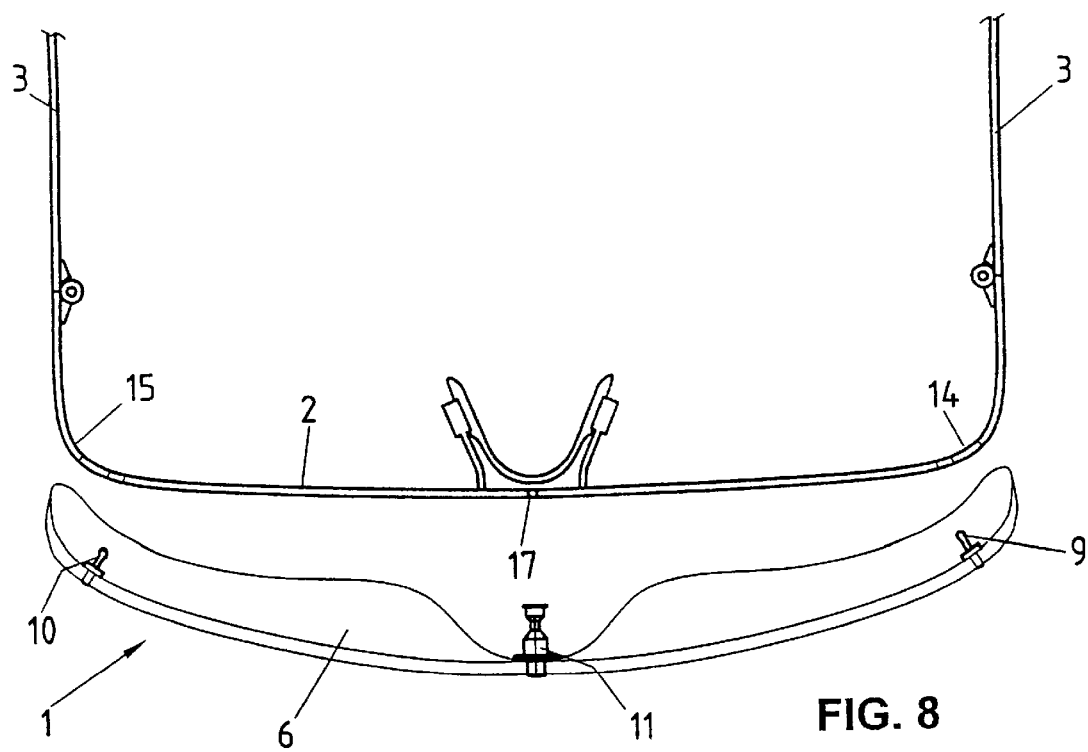
FIG. 8, a view from above of the eyeglasses according to FIG. 7 with protective shield removed.

To place the protective shield 6 on the eyeglasses 1, as can be seen in FIG. 8, the protective shield 6 is led toward the eyeglass frame 2 in such a way that the pins 9 and 10 can penetrate into the lateral, slot-shaped recesses 14 and 15, as has been described with respect to FIGS. 5 and 6. Then the protective shield 6, whose curvature is somewhat larger than that of the eyeglass frame 2, is pressed into the middle area of the eyeglass frame 2 until the second cylindrical part 22 of the central pin 11 comes to be located above the central, slot-shaped recess 17. Afterwards the eyeglass frame 2 and the protective shield 6 are pushed toward each other so that the central pin 11 is introduced into the bore 19 of the central, slot-shaped recess 17 transversely to the longitudinal axis. Then after letting go, the protective shield 6 will spring back so that the third cylindrical part 26 of the central pin 11 is pulled into the bore 19 until the collar 27 abuts on the eyeglass frame 2, as has already been described with respect to FIGS. 2 to 4. The eyeglasses 1 with attached protective shield 6 are shown in FIG. 7. As a result of the pressing together of the protective shield 6 and the eyeglass frame 2, the pins 9 and 10 in the lateral, slot-shaped recesses 14 and 15 shift themselves outwardly; they thus end up in the area whose width is smaller than the diameter of the swelling 33 of the pins 9 and 10, as is shown in FIGS. 5 and 6. In this way pins 9 and 10 are also optimally held on the eyeglass frame 2. By means of the elastic tensioning of the protective shield 6 with respect to the eyeglass frame 2, the protective shield 6 is supported on the eyeglass frame 2 with the flange-shaped supporting portions 31 of the pins 9 and 10, thus achieving a play-free holding of the protective shield 6 on the eyeglasses.

To take the protective shield 6 off the eyeglasses 1, the steps described in the foregoing are carried out in reverse order.

With these eyeglasses with attachable protective shield according to the invention, optimal protection of the eyes is made possible, while making use of the prescription lenses of the eyeglasses at the same time. Such eyeglasses offer not only protection against the sun, but also against splashing or particles, such as shavings, and also against streams of air optimally, while at the same time offering optimal vision. The protective shield can also be provided with recesses so that it can also be used with telescopic lenses, which, for example, can be fixed to the prescription lenses. This means that such eyeglasses with attachable protective shield are especially suitable for use by medical professionals, such as, for example, physicians, dentists and the like. The protective shield can thereby be designed in such a way that is fits optimally with mouth and nose protection.

The protective shield can be attached to, or removed from, the corresponding eyeglasses without any difficulty, the eyeglasses fulfilling optimally the function of purely optical glasses. With the protective shield attached as well as with the protective shield removed, these eyeglasses maintain their aesthetic look.

What is claimed is:

1. Eyeglasses with attachable protective shield comprising:

an eyeglass frame with prescription lenses held in the frame, holding means disposed on the attachable protective shield and on the eyeglass frame, with which means the protective shield is held on the eyeglass frame in front of the lenses and essentially parallel thereto, the protective shield having a curved, outwardly directed, convex surface, wherein the holding means comprise two pins inserted in the protective shield, one each in a lateral edge area, and a central pin, inserted essentially between said two pins, each of the two pins has a swelling on an area remote from the protective shield, and corresponding to the pins inserted in the protective shield one lateral slot-shaped recess in each of the two lateral edge areas of the eyeglass frame and in the middle area one central slot-shaped recess, each lateral slot-shaped recess being provided with an extension, the longitudinal axes of the two lateral, slot-shaped recesses and the two extensions being directed substantially toward one another, and wherein the central slot-shaped recess is disposed substantially transversely with respect to said two lateral slot-shaped recesses are elastically tensioned, and wherein the eyeglass frame and the attachable protective shield are elastically tensioned with respect to each other.

2. Eyeglasses with attachable protective shield according to claim 1, wherein the two pins mounted on the lateral edge areas each consist of a screw portion, a flange-shaped supporting portion and a cylindrical portion, and the swelling adjoining the cylindrical portion is spherical, and wherein the corresponding slot-shaped recess has a width which is smaller than the spherical thickness, whereas the width of the extension is slightly larger and the length of the extension is greater than the diameter of the spherical swelling.

3. Eyeglasses with attachable protective shield according to claim 2, wherein on the side turned away from the protective shield two bores each are made in the flange-shaped supporting part of the two pins mounted on the lateral edge areas of the protective shield.

4. Eyeglasses with attachable protective shield according to claim 1, wherein the central pin consists of a screw part, a flange-shaped supporting part, a first cylindrical part, a tapering first frustum, a second cylindrical part, a widening second frustum and an adjoining third cylindrical part, which is terminated with a collar, and wherein the corresponding central slot-shaped recess is opened in a funnel-shape toward the upper edge of the eyeglass frame, has a narrowing and a bore adjoining the narrowing, the width of the narrowing being slightly larger than the diameter of the second cylindrical part, and the diameter of the bore corresponding approximately to the diameter of the third cylindrical part.

5. Eyeglasses with attachable protective shield according to claim 4, wherein on the side turned away from the protective shield two bores are made in the flange-shaped supporting part of the central pin, fixed to the protective shield.

6. Eyeglasses with attachable protective shield according to claim 1, wherein the protective shield is made of acrylic glass which is clear or tinted.

* * * * *